(12) United States Patent
Li

(10) Patent No.: US 10,617,311 B2
(45) Date of Patent: Apr. 14, 2020

(54) SYSTEM AND METHOD FOR REAL-TIME HEARTBEAT EVENTS DETECTION USING LOW-POWER MOTION SENSOR

(71) Applicant: Samsung Electronics Co., Ltd., Suwon-si, Gyeonggi-do (KR)

(72) Inventor: Yelei Li, Santa Clara, CA (US)

(73) Assignee: Samsung Electronics Co., Ltd. (KR)

( * ) Notice: Subject to any disclaimer, the term of this patent is extended or adjusted under 35 U.S.C. 154(b) by 259 days.

(21) Appl. No.: 15/726,756

(22) Filed: Oct. 6, 2017

(65) Prior Publication Data

US 2019/0046054 A1 Feb. 14, 2019

Related U.S. Application Data

(60) Provisional application No. 62/543,270, filed on Aug. 9, 2017.

(51) Int. Cl.
*A61B 5/024* (2006.01)
*A61B 5/0205* (2006.01)
*A61B 5/11* (2006.01)
*A61B 5/00* (2006.01)
*A61B 5/021* (2006.01)

(52) U.S. Cl.
CPC ........ *A61B 5/02405* (2013.01); *A61B 5/0205* (2013.01); *A61B 5/1118* (2013.01); *A61B 5/02108* (2013.01); *A61B 5/4812* (2013.01); *A61B 5/4818* (2013.01); *A61B 5/681* (2013.01)

(58) Field of Classification Search
CPC . A61B 5/02405; A61B 5/0205; A61B 5/1118; A61B 5/02108; A61B 5/4812; A61B 5/4818; A61B 5/681
See application file for complete search history.

(56) References Cited

U.S. PATENT DOCUMENTS

| 2009/0149779 | A1* | 6/2009 | Russo | A61B 5/02405 600/595 |
| 2011/0066042 | A1* | 3/2011 | Pandia | A61B 5/029 600/484 |
| 2017/0273635 | A1* | 9/2017 | Li | A61B 5/7282 |

* cited by examiner

*Primary Examiner* — Lindsey G Wehrheim
(74) *Attorney, Agent, or Firm* — McAndrews, Held & Malloy, Ltd.

(57) ABSTRACT

As a non-limiting example, various aspects of this disclosure provide embodiments of real-time heartbeat events detection using low-power, low-noise motion sensor.

20 Claims, 11 Drawing Sheets

SYSTEM AND METHOD FOR REAL-TIME HEARTBEAT EVENTS DETECTION USING LOW-POWER MOTION SENSOR

RELATED APPLICATIONS

This application claims the benefit of the United States Provisional Application 62/543,270, filed on Aug. 9, 2017, the disclosure of which is incorporated herein in its entirety by reference. The U.S. application Ser. No. 14/928,072 filed on Oct. 30, 2015, titled "Method for Low-Power-Consumption, Robust Estimation of Cardiovascular Periodicity, Contour Analysis, and Heart Rate," is incorporated herein in its entirety by reference. The U.S. application Ser. No. 15/168,531 filed on Mar. 28, 2016, titled "Method and Apparatus for Heart Rate and Respiration Rate Estimation Using Low Power Sensor," is incorporated herein in its entirety by reference. The U.S. application Ser. No. 15/264,333 filed on Jun. 29, 2016, titled "System and method for Providing a Real-Time Signal Segmentation and Fiducial Points Alignment Framework," is incorporated herein in its entirety by reference.

BACKGROUND

Certain embodiments of the disclosure relate to biometric equipment and more specifically to a system and method for real-time heartbeat events detection using low-power motion sensor.

Limitations and disadvantages of conventional and traditional approaches will become apparent to one of skill in the art through comparison of such systems with some aspects of the present disclosure as set forth in the remainder of the present application with reference to the drawings.

SUMMARY

The present disclosure discloses a system and method for real-time heartbeat events detection using low-power motion sensor, substantially as shown in and/or described below, for example in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF THE DRAWINGS

These and/or other aspects will become apparent and more readily appreciated from the following description of example embodiments, taken in conjunction with the accompanying drawings.

DETAILED DESCRIPTION

Figure 1:
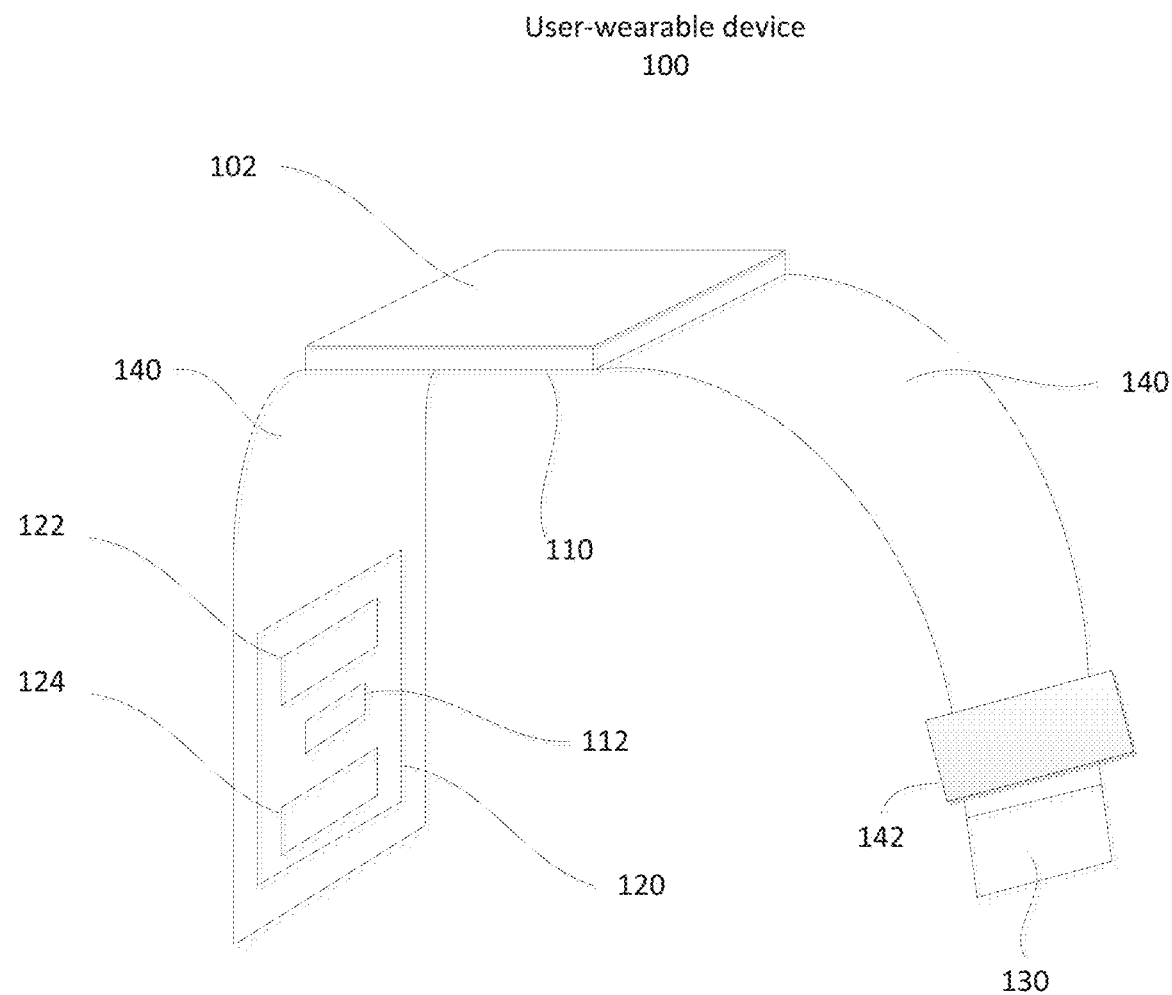
FIG. 1 is a diagram illustrating an electronic device, in accordance with various example aspects of this disclosure.

Various example embodiments of the disclosure will be described in detail with reference to the accompanying drawings such that they can be made and used by those skilled in the art.

Various aspects of the present disclosure may be embodied in many different forms and should not be construed as being limited to the example embodiments set forth herein. Rather, these example embodiments of the disclosure are provided so that this disclosure will be thorough and complete and will convey various aspects of the disclosure to those skilled in the art.

The terminology used here is for the purpose of describing particular embodiments only and is not intended to limit the disclosure. In the drawings, the thickness, width, length, size, etc., of layers, areas, regions, components, elements, etc., may be exaggerated for clarity. Like reference numerals refer to like elements throughout.

As utilized herein, "and/or" means any one or more of the items in the list joined by "and/or." As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y, and/or z" means "one or more of x, y, and z". As utilized herein, the term "exemplary" means serving as a non-limiting example, instance, or illustration. As utilized herein, the terms "e.g." and "for example" set off lists of one or more non-limiting examples, instances, or illustrations.

Also, the singular forms are intended to include the plural forms as well, unless the context clearly indicates otherwise. It will be further understood that the terms "comprises," "comprising," "includes," and/or "including," when used in this specification, specify the presence of stated features, numbers, steps, operations, elements, and/or components, but do not preclude the presence or addition of one or more other features, numbers, steps, operations, elements, components, and/or groups thereof.

In addition, it will be understood that when an element A is referred to as being "connected to" or "coupled to" an element B, the element A can be directly connected to or coupled to the element B, or an intervening element C may be present between the elements A and B so that the element A can be indirectly connected to or coupled to the element B.

Furthermore, although the terms first, second, etc., may be used to describe various members, elements, regions, layers and/or sections, these members, elements, regions, layers and/or sections should not be limited by these terms. These terms are only used to distinguish one member, element, region, layer, and/or section from another. Thus, for example, a first member, a first element, a first region, a first layer, and/or a first section discussed below could be termed a second member, a second element, a second region, a second layer, and/or a second section without departing from the teachings of the present disclosure.

Spatially relative terms, such as "upper," "lower," "side," and the like, may be used for ease of description to describe the relationship of one element or feature to another element(s) or feature(s) as illustrated in the figures. It will be understood that the spatially relative terms are intended to encompass different orientations of the device in use or operation in addition to the orientation depicted in the figures. For example, if the device in the figures is turned upside-down, elements described as "below" or "beneath" other elements or features would then be oriented "above" the other elements or features. Thus, the term "below" can encompass both an orientation of above and below.

Furthermore, a term such as a "module," "block," etc., may comprise hardware and/or software components, and may further comprise other modules/blocks/etc., as well as be a part of a larger module or a block. Generally, the terms "module" and "block" may be interchangeable.

The detailed description set forth below is intended as a description of various example embodiments of a system and method for real-time heartbeat events detection using a low-power motion sensor. Usage of low-power motion sensor for real-time heartbeat events detection may be described in more detail in the U.S. application Ser. No. 15/168,531 filed on Mar. 28, 2016, titled "Method and Apparatus for Heart Rate and Respiration Rate Estimation Using Low Power Sensor."

The description is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features.

According to various embodiments, the present system for detecting heartbeat events may use a motion sensor to provide a signal, and various techniques such as, for example, combined channel selection, cross-correlation, a probability hybrid network operating, etc., may operate on the signal. In this disclosure, a scheduling framework for continuous heartrate and heartbeat events detection using a motion sensor is detailed. A low-power, low-noise motion sensor, which may be a part of, for example, a wrist-worn device such as the user-wearable device 100 described with respect to FIG. 1, configured to detect heartbeat events may increase the battery life of the user-wearable device 100. Additionally, the precision of the beat locations may be increased compared to other embodiments for detecting heartbeats.

FIG. 1 is a diagram illustrating an electronic device in accordance with an embodiment of the present disclosure. Referring to FIG. 1, an electronic device, such as the user-wearable device 100, has a display 102, control block 110, the processor 112, a sensor module 120, a battery 130, a band 140, and a clasp 142. The sensor module 120 may include sensors 122 and 124. The control block 110, the processor 200 (FIG. 2), and/or the processor 112 may also be referred to as a diagnostic processor, and may be able to execute instructions. Accordingly, a diagnostic processor may comprise, for example, a digital signal processor, a controller, a use specific processor, a general processor, and so on. At times, for ease of description, a diagnostic processor may also generally refer to a combination of various hardware.

Although the user-wearable device 100 can be worn on a wrist, various embodiments of the disclosure need not be so limited. The user-wearable device 100 may also be designed to be worn on other parts of the body, such as, for example, on an arm (around the forearm, the elbow, or the upper arm), on a leg, on the chest, on the head like a headband, on the throat like a "choker," and on an ear. The user-wearable device 100 may be able to communicate with other electronic devices such as, for example, a smartphone, a laptop, or various medical devices at a hospital or a doctor's office. This will be described in more detail with respect to FIG. 3.

The display 102 may output monitored physiological signals from the user's body for viewing by the user and/or others. The signals being monitored may be referred to as biosignals or biometric data. The monitored signals may be, for example, heart (pulse) rate, pulse morphology (shape), pulse spacing (inter-beat intervals), respiration (breathing) rate, and blood pressure. The display 102 may also output instructions to the user or others in the use of the user-wearable device 100 or use of other measurement devices, as well as status and diagnostic results, for example.

The control block 110 can receive the monitored signals via a sensor in the sensor module 120. The sensor module 120 may include, for example, the sensors 122 and 124 that may acquire signals from the user's wrist when the user-wearable device 100 is worn by a user, as well as provide other information that may indicate the user's body position, motion, and the like. The sensor 122 and/or 124 may be, for example, an accelerometer, a gyroscope, piezoelectric device, an optical sensor such as, for example, a camera, a sensor using sonic frequencies, and the like. The processor 112 may control the sensors 122 and 124, and may also process the signals monitored by the sensors 122 and 124. Various embodiments of the disclosure may have the control block 110 also perform the functions of the processor 112. Various embodiments of the disclosure may also have different number of sensors.

The sensor 122 may be used, for example, to monitor motion. The sensor 124 may be similar to the sensor 122 or a different type of sensor such as, for example, a thermometer for taking the user's temperature. Various embodiments of the disclosure may include different numbers of sensor modules. For example, some embodiments may only have one sensor module, while other embodiments may have 2 or more sensor modules.

The battery 130 is configured to provide power for the user-wearable device 100. The battery 130 may be charged using a wired charging system or a wireless charging system.

The band 140 may be wrapped around a wrist and the user-wearable device 100 may be held on the wrist by using the clasp 142.

Figure 2:
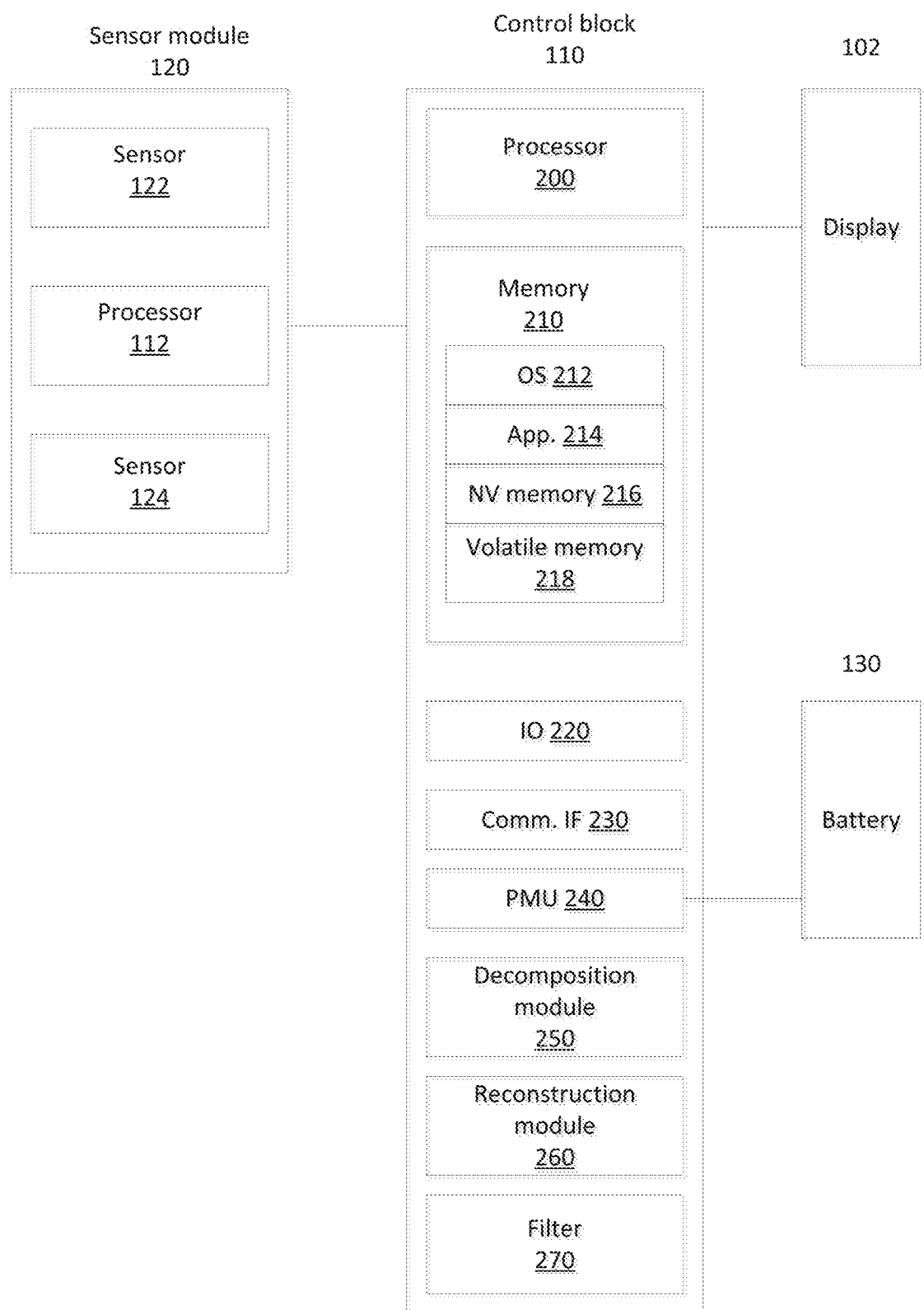
FIG. 2 is a high-level block diagram of an electronic device, in accordance with various example aspects of this disclosure.

FIG. 2 is a high-level block diagram of an electronic device in accordance with an embodiment of the present disclosure. Referring to FIG. 2, there is shown the display 102, the control block 110, the sensor module 120, and the battery 130. Output to the display 102 can be controlled, for example, by the control block 110. The display 102 may also include input devices (not shown) such as, for example, buttons, dials, touch sensitive screen, and microphone.

The control block 110 may include a processor 200, memory 210, an input/output (IO) interface 220, a communication interface 230, a power management unit (PMU) 240, a decomposition module 250, a reconstruction module 260, and a filter 270. While the control block 110 is described as including these various devices, other embodiments may use other architectures where the different functionalities are grouped differently. For example, the grouping may be in different integrated circuit chips. Or the grouping may be combining different devices such as the IO interface 220 and the communication interface 230 together, or the decomposition module 250 and the reconstruction module 260 together.

The processor 200 may control operation of the sensor module 120 as well as receive monitored signals from the sensor module 120. The processor 200 may control the user-wearable device 100, including processing the monitored signals from the sensor module 120, displaying the processed signals on the display 102, receiving input from the display 102, interfacing with various devices via the IO interface 220 or the communication interface 230 by executing instructions in the memory 210. The TO interface 220 may be used by the processor 200 to interface with the display 102.

The processor 112 may operate using different architectures in different embodiments. For example, the processor 112 may use the memory 210 to store instructions to execute, or the processor 112 may have its own memory (not shown) for its instructions. The processor 112 may also have other functionalities found in the control block 110. Although some embodiments have separate processors 200 and 112, the various embodiments need not be limited so. There may be one control block 110 that controls the functionality of the user-wearable device 100, or there may be multiple processors for the user-wearable device 100.

The memory 210 may include non-volatile memory 216 and volatile memory 218. The operating system and applications may be stored in the non-volatile memory 216. Various embodiments of the disclosure may use different memory architectures that are design and or implementation dependent.

The communication interface 230, which comprises a transceiver, may allow the user-wearable device 100 to communicate with other devices via, for example, a wired or wireless protocol such as USB, Bluetooth, Near Field Communication (NFC), and WiFi. The PMU 240 may control receiving power from an outside source, charging the battery 130, as well as allocation of power to the different parts of the user-wearable device 100.

The decomposition module 250 may function to decompose, for example, an input signal such as a BCG signal to multiple frequency bands using time-frequency transforms. The reconstruction module 260 may function to reconstruct, for example, the decomposed signals from the decomposition module 250 to refine and access desired components of the original signal such as the BCG signal. Accordingly, the functions of the decomposition module 250 and the reconstruction module 260 may be performed by, for example, a processor and/or specialized hardware devices. The hardware devices may be off-the-shelf or designed as, for example, an integrated circuit, ASIC, FPGA, etc. For convenience, the decomposition module 250 and the reconstruction module 260 may together be referred to as a transform module. Decomposition and reconstruction of a signal is explained in more detail in the U.S. application Ser. No. 14/928,072. The filter 270 may be used to select specific frequencies from a signal. For example, the filter 270 may be a low-pass filter, a bandpass filter, a high-pass filter, etc., that may attenuate certain frequencies.

Figure 3:
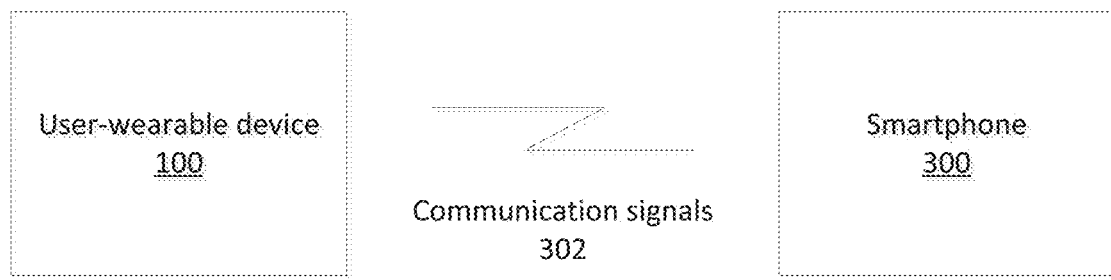
FIG. 3 is an illustration of an electronic device in a communication network, in accordance with various example aspects of this disclosure.
Figure 4A:
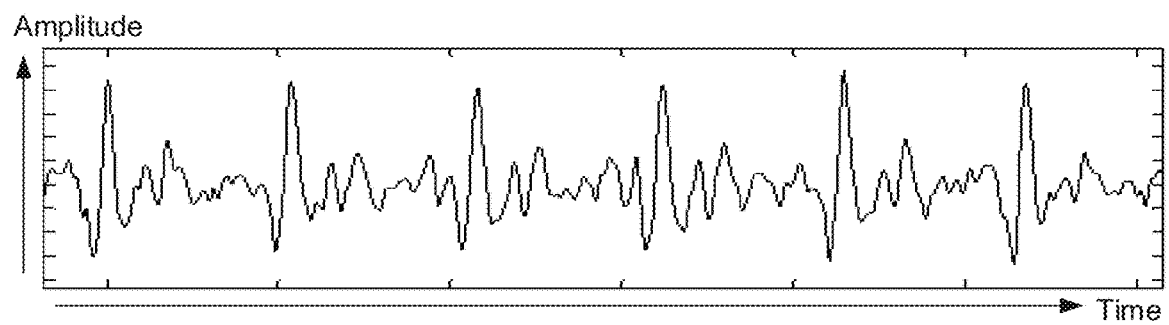
FIGS. 4A-4D illustrate output waveforms of an accelerometer for different positions of an accelerometer at different periods of time, in conjunction with use of various example aspects of this disclosure.
Figure 4B:
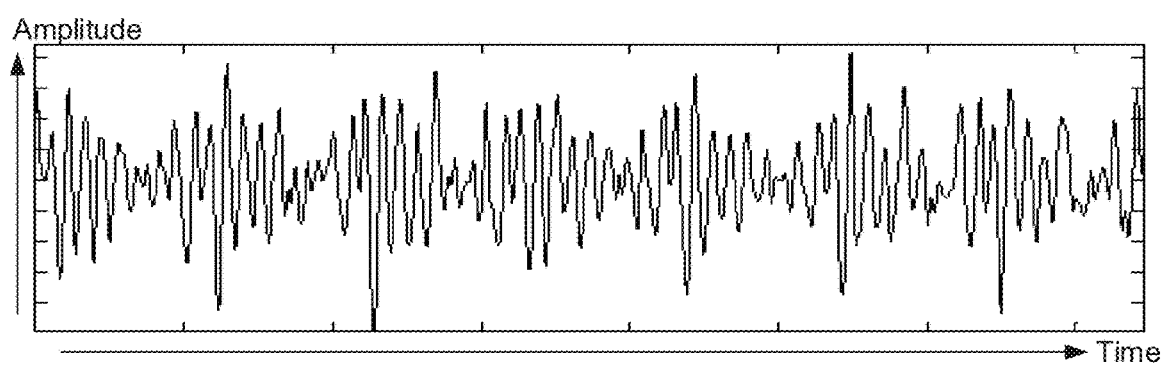
Figure 4C:
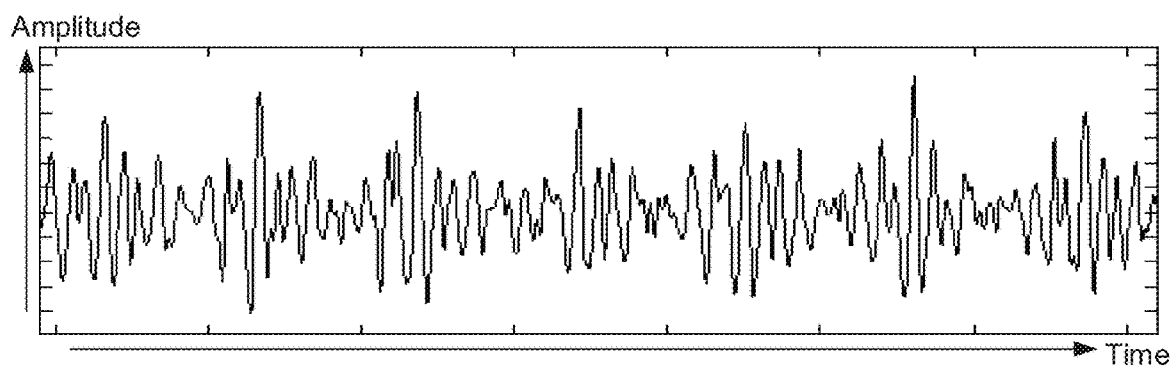
Figure 4D:
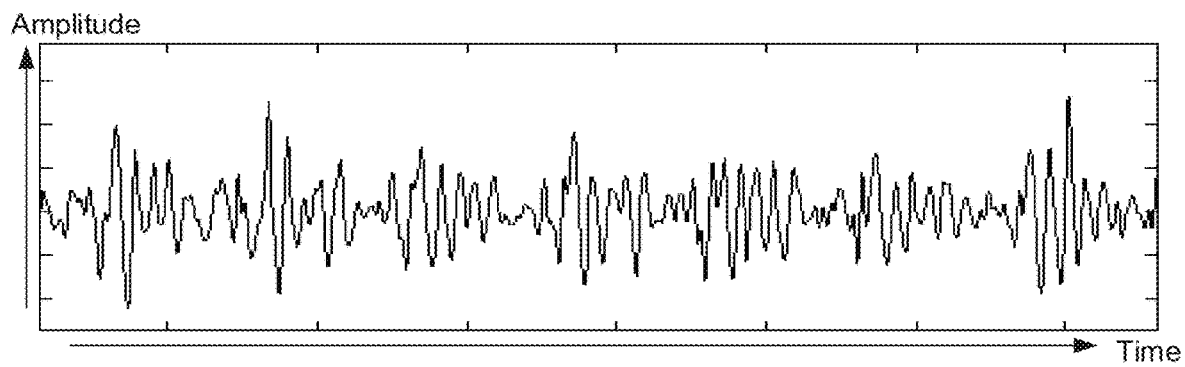

FIG. 3 is an illustration of an electronic device in a communication network in accordance with an embodiment of the present disclosure. Referring to FIG. 3, there is shown the user-wearable device 100 and a smartphone 300. The user-wearable device 100 may communicate with the smartphone 300 using the communication interface 230. The communication may be via the communication signals 302, where the communication may be direct between the user-wearable device 100 and a smartphone 300, or include other elements between the user-wearable device 100 and a smartphone 300.

One of the applications 214 of the user-wearable device 100 may allow the smartphone 300 to control at least some operation of the user-wearable device 100. For example, user-wearable device 100 may output to the display 102 a result of the processing by the control block 110, and/or the same result may be transmitted to the smartphone 300. The user may also select an option either on the user-wearable device 100 or on the smartphone 300. The options may be, for example, to start a biosignal monitoring process by the user-wearable device 100 or to stop the biosignal monitoring process.

Since the smartphone 300 has a larger display, it can be easier for the user to view a result or to select an option on the smartphone 300 rather than on the user-wearable device 100. However, it should be noted that the smartphone 300 may not generally be necessary for operation of the user-wearable device 100.

Heart rate and heartbeat are conventionally detected using an electrocardiogram (ECG) or photoplethysmogram (PPG). An ECG utilizes electrical activity and requires multiple leads positioned at different points on the body. A PPG takes optical measurements of light absorption using a pulse oximeter. Placing multiple electrodes on a user's body may be impractical for wearable applications such as, for example, the user-wearable device 100. Similarly, PPG may also be problematic for wearable devices such as the user-wearable device 100 due to its relatively high power requirements.

Ballistocardiography (BCG) measures body acceleration caused by cardiac output as well as respiration. BCG contains multiple peak events during one heartbeat. These peaks can be categorized into three major groups: pre-systolic, systolic, and diastolic. Systolic waves may correspond to QRS complexes in ECG signal, and they may be a salient features of BCG. BCG signals, however, may also include a wide variety of peaks due to frequency position (orientation) changes as well as level of stability of the measured subject.

In wearable applications, it may be possible to take BCG measurements using one or more motion sensors such as, for example, an accelerometer of the user-wearable device 100. However, it may be useful to take into account the movements of the user wearing the user-wearable device 100 as these movements may act as noise to the BCG measurements. This may be especially true if the user-wearable device 100 is worn on a user's wrist, which may be prone to sudden and unexpected motions.

Accordingly, various embodiments of the disclosure may describe a system for detecting heartbeat events using a motion sensor using one or more of combined channel selection, cross-correlation, and a probability hybrid network. By using a low-power, low-noise motion sensor to detect heartbeat events, the battery life of the device may be significantly extended. Additionally, the precision of the beat locations may be increased.

Various embodiments described below may require less power and yet provide higher precision compared to, for example, an optical approach such as a PPG device, and, yet, when the user is stationary, may prove to be more flexible compared to an ECG device since the disclosed algorithm may enable heartbeat event detection at various body locations or even remote locations without having to have multiple leads positioned at different points of the user's body.

BCG waveforms may vary as the orientation of the motion sensor changes. For example, in one embodiment, the sensor module 120 in the user-wearable device 100 may comprise a sensor 122 that may be a 3-axis accelerometer. BCG signals from the 3-axis accelerometer may vary whenever the orientation of the accelerometer changes. This can be seen in FIGS. 4A-4D, where an accelerometer outputs the waveforms shown in FIGS. 4A-4D for different positions of the accelerometer at different periods of time.

Various embodiments of the disclosure may comprise hardware and software modules that operate to identify artifacts in outputs of a 3-axis accelerometer to generate a heartbeat signal. The artifacts may be caused by, for example, motion of the user-wearable device 100, muscle contraction of the body part that the user-wearable device 100 is on, etc. The artifacts may also be due to false information produced in the heartbeat detection.

Additionally, BCG channel fusion/selection may involve performing in real time, data fusion for the signals output by the 3-axis accelerometer or switching to a different one of the three channels depending on which channel is determined to be the best candidate. Accordingly, various embodiments of the disclosure may provide heartbeat events by optimizing the output signals of the 3-axis accelerometer.

Figure 5A:
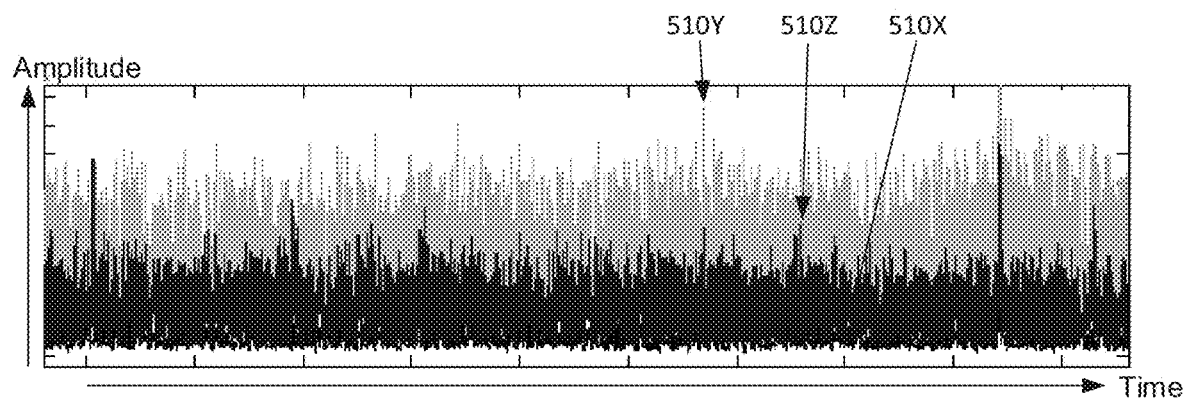
FIGS. 5A-5B illustrate generating an accurate BCG based heartbeat events detection approach with channel optimization, in accordance with various example aspects of this disclosure.
Figure 5B:
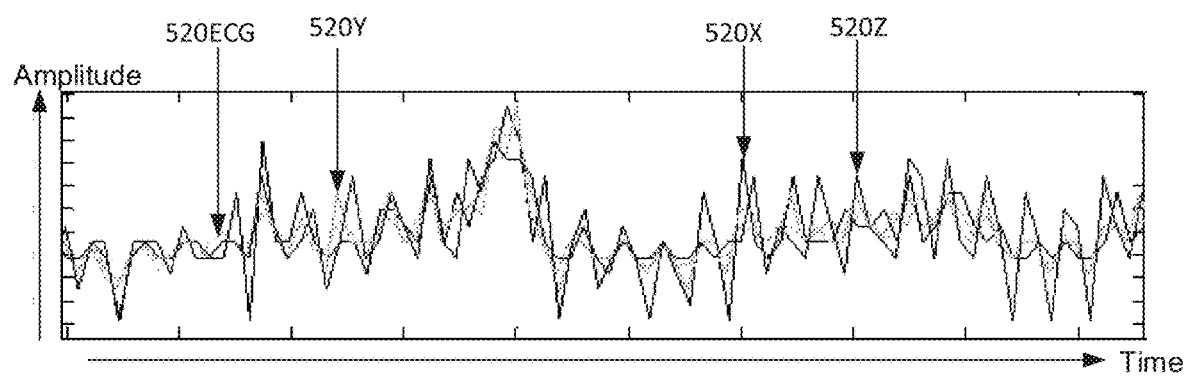

FIGS. 5A-5B illustrate generating an accurate BCG based heartbeat events detection approach with channel optimization, in accordance with various example aspects of this disclosure. Referring to FIG. 5A, there are shown signals that correlate to output signals of the three axes of the accelerometer. For example, 510X may correlate to the X-axis signal, 510Y may correlate to the Y-axis signal, and 510Z may correlate to the Z-axis signal. FIG. 5A shows energy entropy signal of each accelerometer channel as outputs of a BCG reconstruction block. Referring to FIG. 5B, there are shown the X, Y, and Z signals after channel optimization and removal of artifacts. For example, 520X may be the optimized X-axis signal, 520Y may be the optimized Y-axis signal, and 520Z may be the optimized Z-axis signal. FIG. 5B may show enlarged inter-beat interval (IBI) trend for the optimized X, Y, and Z signals compared to an ECG reference IBI signal. An embodiment for optimizing signals is shown in FIG. 5C.

Figure 5C:
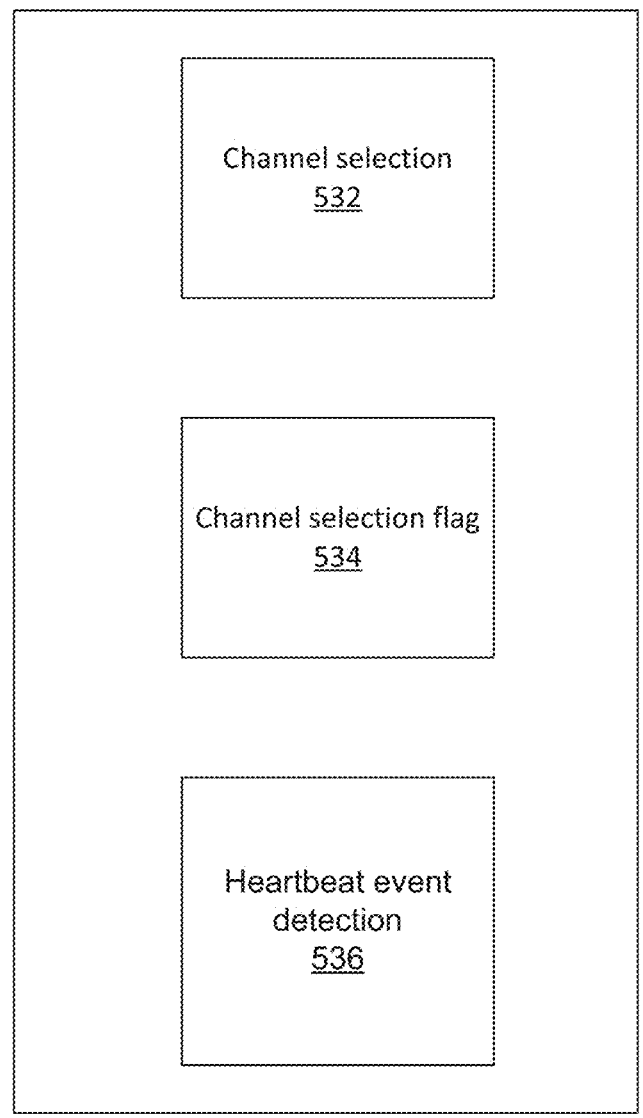
FIG. 5C is an example block diagram for optimizing signals from a 3-axis accelerometer, in accordance with various example aspects of this disclosure.
Figure 6A:
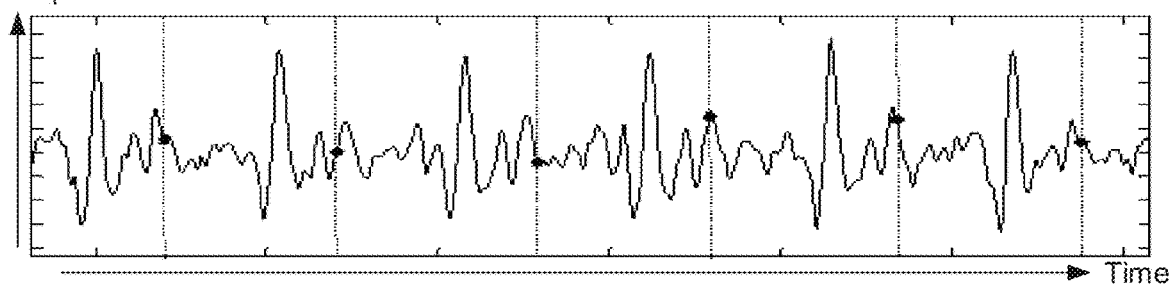
FIGS. 6A-6D illustrate example BCG segmentation results for different signal morphologies, in accordance with various example aspects of this disclosure.
Figure 6B:
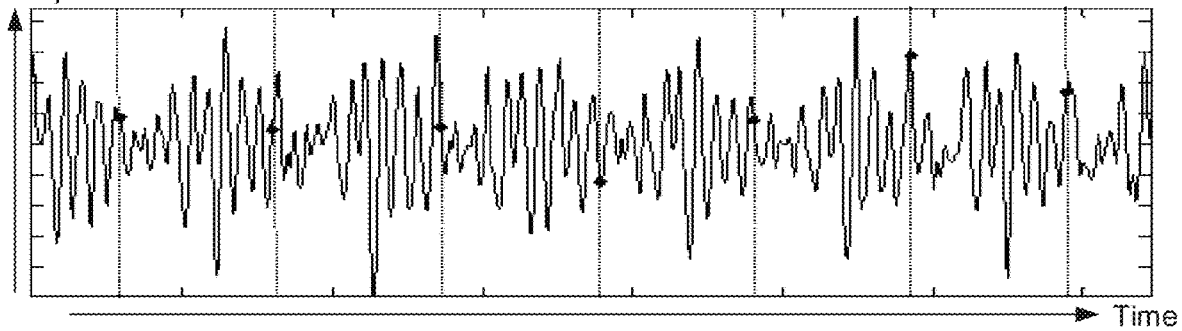
Figure 6C:
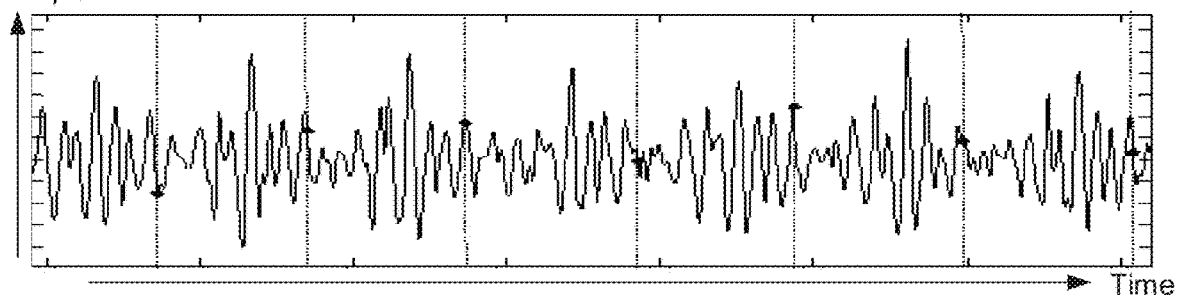
Figure 6D:
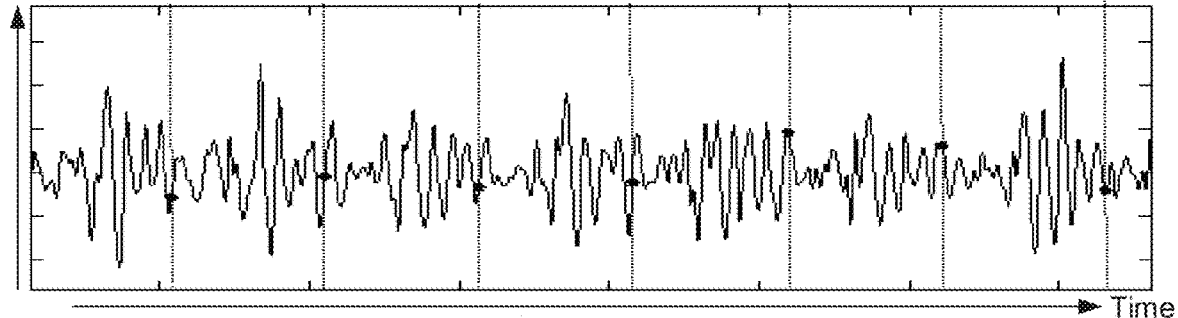

FIG. 5C is an example block diagram for optimizing signals from a 3-axis accelerometer, in accordance with various example aspects of this disclosure. Referring to FIG. 5C, there is shown an optimizing block 530 comprising a channel selection block 532, a channel selection flag block 534, and a heartbeat event detection block 536. The optimizing block 530, the channel selection block 532, the channel selection flag block 534, and/or the heartbeat event detection block 536 may be logical blocks, and, therefore, may comprise hardware and/or software blocks. The optimizing block 530 may be, for example, a part of the sensor module 120 and/or the control block 110.

In one embodiment of the disclosure, a channel may be selected by the channel selection block 532 based on the signal quality from each of the three axes of the accelerometer. As stated above, FIG. 5A shows energy entropy signal of each accelerometer channel as outputs of BCG reconstruction block. The channel selection block 532 may select the channel with, for example, the highest entropy amplitude since the highest entropy amplitude channel may tend to correlate with the highest alignment with a reference such as, for example, the ECG reference IBI signal. While various entropy values may be used for selection, some embodiments of the disclosure may use, for example, an average entropy value over a window (period) of time. According to an embodiment of the disclosure, the window of time may be fixed or variable based on parameters such as, for example, previous entropy values, amount of prior movements, durations of prior movements, etc.

Various methods for quantifying channel amplitude may be used. For example, the channel amplitude may be determined by integrating over the window of time. Other embodiments may use alternative method(s) to quantify periodicity feature of each candidate channel to select a best candidate channel.

The channel selection flag block 534 may provide a capability of switching among channels when activity is detected in the system. As described above, BCG signals (output waveforms) may vary even with slight position change. Accordingly, when the device for detecting heartbeat is the user-wearable device 100 that is worn on a wrist, the BCG morphology may change whenever a subject's hand moves. Accordingly, in an embodiment, the channel selection flag may be set to 1 when an average entropy value of the current optimal sensor channel goes below, for example, a triggering threshold. The channel selection flag may then be used to select a next candidate channel that may have a higher entropy amplitude. At times, there may not be, for example, a better candidate channel, and, accordingly, the present channel may be kept. Various embodiments may also allow for the average entropy value to be below the triggering threshold for a set amount of time before setting the channel selection flag.

The heartbeat event detection block 536 may comprise a detection framework based on cross-correlation calculation for real-time embedded system implementation as well as computational efficiency. However, it may be noted that other technologies may also be used in addition to, or in place of the cross-correlation calculation detection framework.

FIGS. 6A-6D illustrate example BCG segmentation results for different signal morphologies, in accordance with various example aspects of this disclosure. Referring to FIGS. 6A-6D, there are shown results of using time-delay embedding (TDE) beat detection for a BCG signal. The FIGS. 6A-6D may correspond to, for example, the FIGS. 4A-4D. The BCG signals may be segmented into clips referring to segmentation locations of this block as shown by the vertical lines in FIGS. 6A-6D. The U.S. application Ser. No. 15/264,333 filed on Jun. 29, 2016, titled "System and method for Providing a Real-Time Signal Segmentation and Fiducial Points Alignment Framework," describes TDE beat detection and segmentation in more detail.

Figure 7:
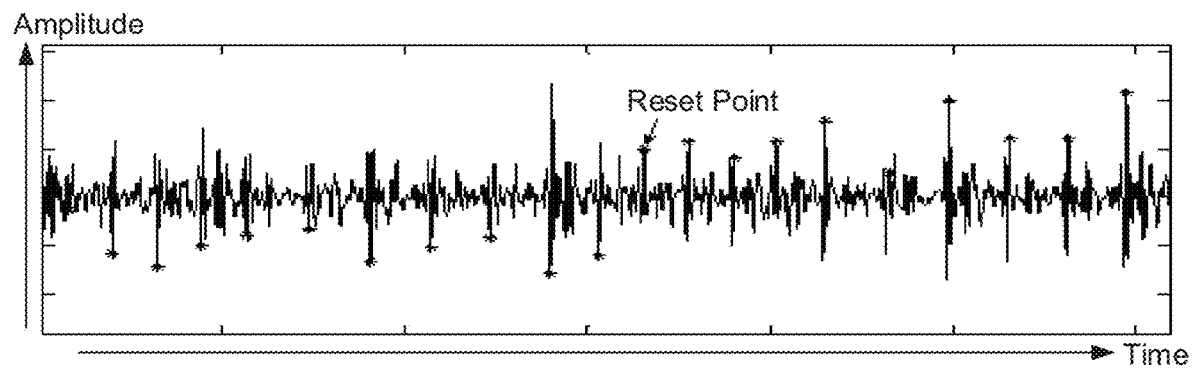
FIG. 7 illustrates an example BCG heartbeat event detection with a reset flag based on correlation between segments, in accordance with various example aspects of this disclosure.

FIG. 7 illustrates an example BCG heartbeat event detection with a reset flag based on correlation between segments, in accordance with various example aspects of this disclosure. Referring to FIG. 7, there is shown a BCG waveform that is segmented, where the segment boundaries may be indicated by vertical lines. For two adjacent BCG segments, cross-correlation may be calculated and alignment points identified based on maximum correlation index. If the correlation is below a preset threshold or energy of a selected peak is too low, then a peak allocation flag may be triggered and fiducial peak may be reset for the next segment as indicated by the label "Reset point." The reset flag may help prevent feature point drift. A peak may be identified as the point with highest energy of a given segment. In most cases, J peak is the most salient feature point in BCG signal.

As shown in FIG. 7, a peak allocation reset may be triggered in the middle of the plot due to low correlation between segments. A reset flag may then be able to provide additional valuable information such as, for example, BCG signal quality and confidence indicator.

A BCG period with frequent resets may indicate low BCG signal quality or inconsistent BCG morphology. The BCG signal quality may vary for different sleeping stages, for example, due to muscle contraction and other artifacts. Accordingly, the reset flag may be used as sleeping staging factor. In another embodiment, sleep apnea symptoms such as snoring may also cause signal quality degradation. Accordingly, the reset flag may be used to quantify sleep apnea as well as sleep quality.

Heartbeat events information may be further used to calculate biometrics such as, for example, heart rate variability (HRV), stress, cardiac arrhythmia detection, etc. The reset flag may help to identify reliable segments and exclude periods with low quality confidence.

Figure 8:
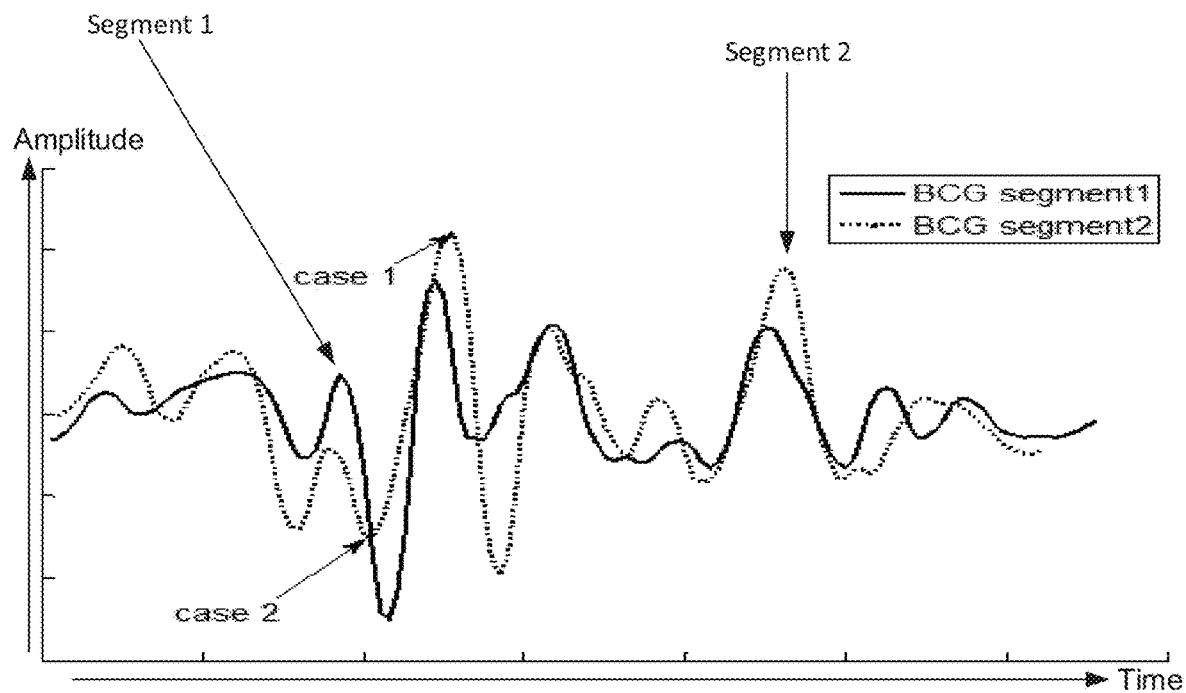
FIG. 8 illustrates an example BCG segment cross-correlation alignment, in accordance with various example aspects of this disclosure.

FIG. 8 illustrates an example BCG segment cross-correlation alignment, in accordance with various example aspects of this disclosure. Referring to FIG. 8, there are shown two adjacent BCG segments Segment1 and Segment2 that are aligned based on cross-correlation. For case 1, if the positive peak of the BCG Segment1 is the heartbeat event, and the corresponding heartbeat event of BCG Segment2 may be identified as the primary positive peak close to the prior segment peak. Similarly, for case 2, a negative peak of BCG Segment2 may be selected as the closest negative peak of the heartbeat event of BCG Segment1. Accordingly, it can be seen that if the reset flag is not triggered, heartbeat event of current BCG segment may be determined based on event information of the prior BCG segment.

In some embodiments, a signal filtering block may be used to remove high frequency noise from the BCG segments, for example, to avoid identifying false peaks caused by noise and further preventing feature point drift.

As discussed above, BCG heartbeat events may provide valuable cardiac information for downstream algorithms. In some applications, multiple fiducial feature points may be acquired from a single BCG segment. In one embodiment, BCG heartbeat event information may be used for blood pressure calculation. For example, quantitative relationship of multiple BCG feature points may be useful in modeling blood flow activity. Accordingly, the proposed framework may be easily extended to identify multiple event locations using a similar mechanism.

While some embodiments of the disclosure may have been disclosed, various embodiments need not be so limited. For example, while a BCG heartbeat event detection block was described as applying cross-correlation to quantify similarity between two adjacent BCG segments, there may be other options to achieve a similar goal.

Furthermore, an entropy based approach was used to reconstruct BCG signal. However, a transform block may use other approaches such as, for example, neural-network approximation.

Channel selection may be done by, for example, alternative approaches that quantify BCG signal quality.

BCG heart event detection may also not be limited to signal point detection. Other methods may comprise, for example, multiple event locations in a single segment or morphological variation of corresponding fiducial points between adjacent segments.

Figure 9:
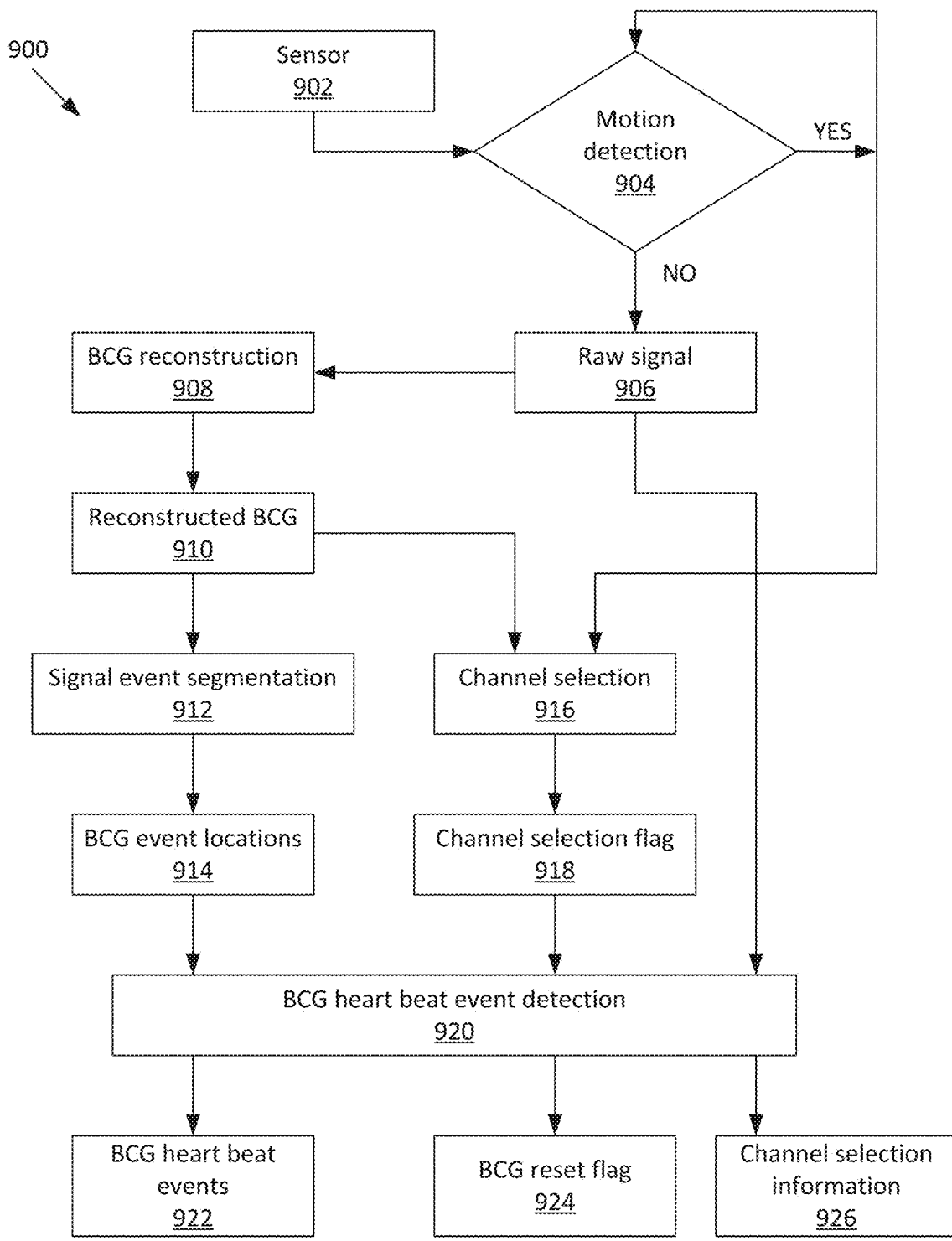
FIG. 9 illustrates an example flow diagram for BCG heartbeat event detection, in accordance with various example aspects of this disclosure.

FIG. 9 illustrates an example flow diagram for BCG heartbeat event detection, in accordance with various example aspects of this disclosure. Referring to FIG. 9, there is shown a flow diagram 900 that describes processing signals by a present example system. The raw signals (biosignals) to be processed may be received from a wearable device such as, for example, a user-wearable device 100. The user-wearable device 100 may detect the raw signals (biosignals) via the sensor module 120.

At block 902, the present example system may receive raw motion signals (biosignals) from a user via, for example, the sensor module 120. A motion sensor such as, for example, an accelerometer on the sensor module 120 may monitor/detect user motion to provide the raw signals. A motion sensor may provide multiple channels of information. For example, a 3-axis accelerometer may provide 3 channels of raw motion signals. When multiple sensors are used, there may be one or more channels of information from each of the sensors.

At block 904, the raw signals may be processed to detect motion. The processing may be via a processor such as, for example, the processor 112 and/or 200. The processing may also be done by hardware mechanisms in place of or in addition to the processor 112 and/or 200.

While some biosignals may not be affected by user motion, other monitored biosignals provide better signals when the user is substantially stationary. For example, BCG signals may provide more reliable signals when the user is substantially stationary. Accordingly, BCG signals (raw motion signals) may be monitored for motion activity, and when the user motion activity is at or above a pre-determined threshold level, the process may loop back to block 904, and also signal to block 916 that excessive motion was detected. The signaling may be, for example, an on state that indicates excessive motion, and an off state that indicates acceptable motion. Other embodiments may have the signaling be, for example, a flag or a pulse that takes place when excessive motion is detected and then the motion level returns to an acceptable level.

Various embodiments may have, for example, the user motion be above the pre-determined threshold for a first period of time before taking action such as blocking the signals and/or signaling block 916, and/or have the user motion be below the pre-determined threshold for a second period of time before taking action. The first period of time may be the same as the second period of time.

When the user motion is below the pre-determined threshold, the biosignal from the sensor may be accepted for processing, and the process may proceed to block 906 by passing, for example, all three channels of signals sensed by the sensor at block 902. This step may be optional in some embodiments with respect to continuing to block 906. For example, some embodiments may transmit the raw signal(s) from the sensor at block 902 and proceed to block 906 without taking into account user motion, while still signaling to block 916. Some embodiments may remove block 904 altogether, thereby going directly from block 902 to block 906, with no signaling being provided to block 916.

At block 906, all the raw signal(s) sensed by the sensor at block 902 may be provided to the BCG reconstruction block at block 908 and the BCG heartbeat event detection at block 920. At block 908, the BCG reconstruction block may use, for example, the decomposition module 250 to decompose the raw signals. The reconstruction module 260 may be used, for example, to reconstruct the decomposed signals to refine and access the desired components of, for example, the original signal such as the BCG signal. Decomposition and reconstruction of a signal is explained in more detail in the U.S. application Ser. No. 14/928,072. The filter 270 may be used to select specific frequencies from a signal.

BCG reconstruction is described as comprising the decomposing and reconstruction functions for the sake of expedience. The decomposition and reconstruction may occur for each channel of raw sensor signal from sensed by the sensor(s) at block 902.

At block 910, the reconstructed BCG signals are provided for signal event segmentation at block 912 and channel selection at block 916. At block 912, the signal event segmentation function may further process the BCG signal for signal event segmentation based on, for example, TDE beat detection. The TDE approach may produce robust beat locations for different morphological variations of a given signal. At block 914, the BCG event locations function may identify specific events in the BCG signal segments.

At block 916, the channel selection function may use the excessive motion signal from block 904 to determine whether a channel selection flag needs to be set. The channel selection flag may be set to a 1 when the excessive motion signal goes from true to false. Additionally, the channel selection flag may be set to a 1 upon first starting the process of detecting the heart beat events when the excessive motion signal is false. Accordingly, an embodiment of the disclosure may set the channel selection flag at block 918 to a 1 to select a new channel when the motion level settles down to an acceptable level. This may be to indicate that BCG data is available again, so a channel can be selected for BCG heart beat event detection at block 920.

Additionally, the channel selection function at block 916 may also determine whether the signal from the presently selected channel from block 910 has dipped below a threshold for signal acceptability. If so, the channel selection flag may also be set to a 1. If not, the channel selection flag is reset to a 0. Some embodiments may look at the presently selected channel from block 910 in determining whether the channel selection flag should be set. Other embodiments may look at the presently selected channel as well as compare it to other channels from block 910 before determining whether the channel selection flag should be set.

Various embodiments may control the channel selection flag to take into account a plurality of conditions. For example, when the channel selection flag is set due to a signal from block 904, it may be reset, for example, after a new channel has been selected at block 920. Accordingly, the channel selection flag may not be reset just due to a state of the input from block 910.

The inputs received from blocks 914, 918, and 906 are then processed by the BCG heartbeat event detection function at block 920. For example, when the channel selection flag is set to 1, a next candidate channel that may have a higher entropy amplitude may be selected. At times, there may not be, for example, a better candidate channel, and, accordingly, the present channel may be kept. The entropy amplitude may be determined, for example, based on window-based quantification as disclosed with respect to FIG. 5.

The outputs of the BCG heartbeat event detection block may be received as BCG heartbeat events at block 922, BCG reset flag at block 924, and channel selection information at block 926.

Various embodiments may allow different functionalities to be performed at different blocks. For example, in an embodiment, block 918 may select the channel to be used, and block 918 may send a channel indication to block 920 so that block 920 can use the appropriate channel for BCG heart beat event detection. Other embodiments may allow, for example, block 918 to select the channel, and then communicate the selected channel to one or more of the blocks 912, 914, and 920 so that those blocks may only perform operations on the selected channel. Accordingly, it can be seen that many different rearrangements of functionalities are possible.

Figure 10:
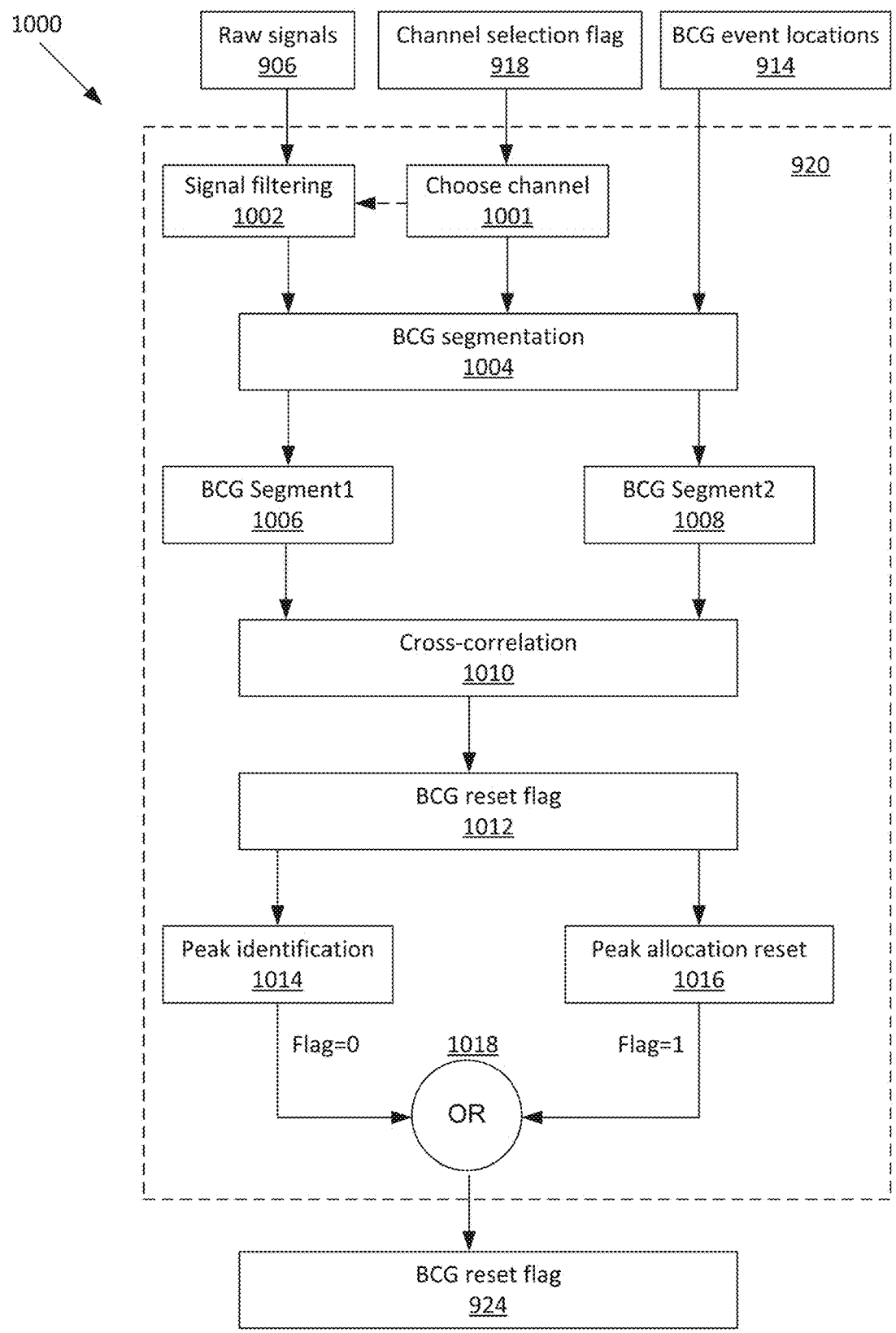
FIG. 10 illustrates an example of a detailed description of the BCG heartbeat event detection block, in accordance with various example aspects of this disclosure.

FIG. 10 illustrates an example of a detailed description of the BCG heartbeat event detection, in accordance with various example aspects of this disclosure. Referring to FIG. 10, there is shown a flow diagram 1000 that further describes processing signals by the BCG heartbeat event detection at block 920 of FIG. 9.

The raw signals from block 906, such as, for example, the three raw signals sensed by a 3-axis motion sensor at block 902, may be received by the signal filtering function at block 1002. The channel select flag from block 918 may be received by the choose channel function at block 1001. The chosen channel may then be communicated to block 1004. Various embodiments may also communicate the chosen channel to block 1002. Accordingly, block 1002 may filter the signal from only the chosen channel, and the filtered signal may be provided to the BCG segmentation function at block 1004, along with the BCG event locations from the BCG event locations function at block 914. If the chosen channel is not communicated to block 1002, then all raw signals may be filtered, and the appropriate filtered signal may be used at block 1004.

The BCG segmentation function at block 1004 may determine the segments for the filtered signal corresponding to the chosen channel, for example, using the appropriate BCG event locations corresponding to the chosen channel. Accordingly, a first segment may be output to the BCG Segment1 function at block 1006 and a second segment adjacent to the first segment may be output to the BCG Segment2 function at block 1008. The cross-correlation function may cross-correlate at block 1010 the events of the first segment to the second segment. If the correlation is below a preset threshold or energy of a selected peak is too low, then a peak allocation flag may be triggered and fiducial peak may be reset at block 1012 for the second segment. The reset flag may help prevent feature point drift. A peak may be identified as the point with highest energy of a given segment. In most cases, J peak may be the most salient feature point in BCG signal.

Accordingly, the peak may be identified in the second segment with respect to the first segment at block 1014 if the peak allocation flag is a 0. If the peak allocation flag is a 1, then the peak may be reset at block 1016 so that the peak may be identified for the next segment without comparing it to the previous segment. Depending on the value of the peak allocation flag, the identified peak at block 1014 or the reset fiducial peak at block 1016 may be output at block 1018.

Although some outputs are not shown, an output at block 1018 may be the BCG reset flag.

Figure 11A:
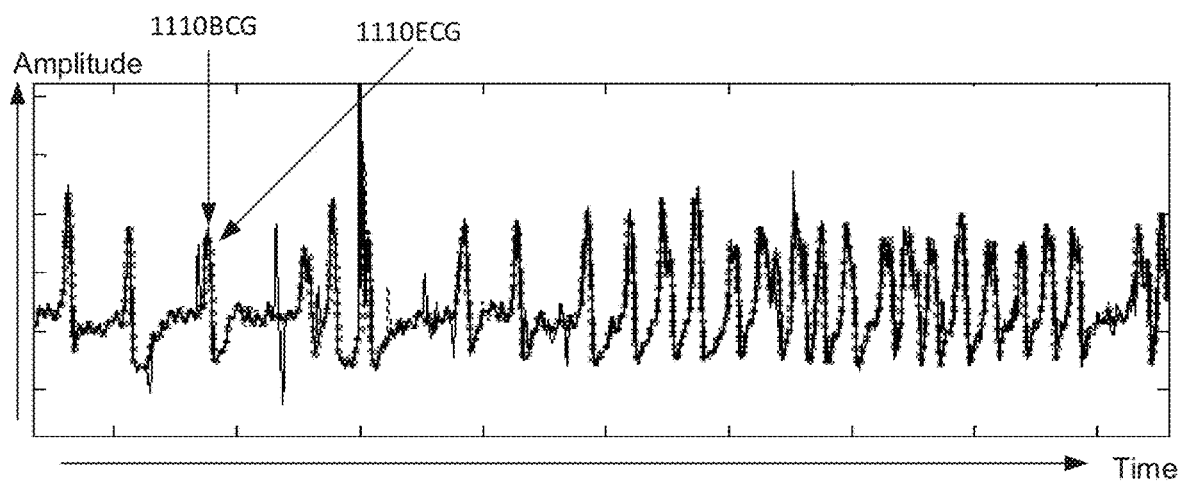
FIGS. 11A-11C illustrate BCG and ECG reference IBI comparison with optimal channel selection results, in accordance with various example aspects of this disclosure.
Figure 11B:
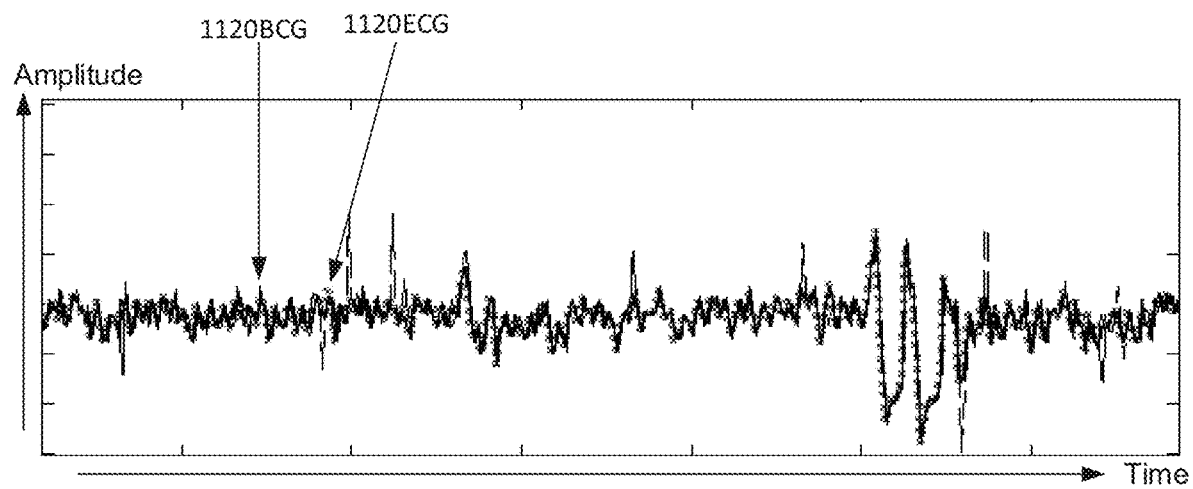
Figure 11C:
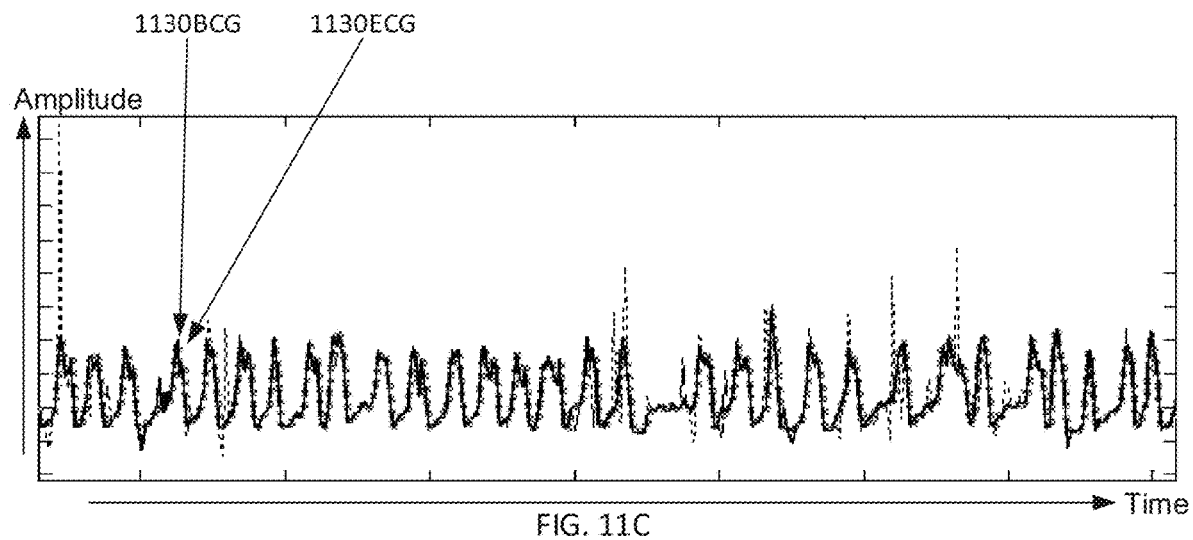

FIGS. 11A-11C illustrate BCG and ECG reference IBI comparison with optimal channel selection results, in accordance with various example aspects of this disclosure. As can be seen in FIGS. 11A-11C, for various morphologies of the BCG signals, the BCG signal tracks the ECG reference IBI signal very well using the process described previously, including the process described with respect to FIGS. 9 and 10.

The various functions/operations in the blocks described with respect to FIGS. 9 and 10 may comprise hardware and/or software modules, and may be found, for example, in the sensor module 120 and/or the control block 110. The software modules may comprise instructions that may be executed, for example, by the processor 112 and/or the processor 200, or other processors that may be used by, for example, the user-wearable device 100. A hardware module may include various types of circuitry that may be used for a specific functionality. For example, the circuitry may be in a custom designed IC (including ASIC, FPGA, etc.) or an off-the-shelf part suitable for the functionality.

Various embodiments of the disclosure may include a method for an electronic device that comprises receiving, via at least one motion sensor, channels of raw motion signals for a user, monitoring the channels for motion activity, and selecting a present channel based on the motion activity. The method may further comprise performing BCG reconstruction for the raw motion signals, determining BCG event locations from the raw motion signals, generating BCG segments from the raw motion signals using the BCG event locations, and cross-correlating, for the present channel, a first BCG segment to a second BCG segment. The first BCG segment may be one of the BCG segments for the present channel, the second BCG segment is another of the BCG segments for the present channel, and the second BCG segment is immediately after the first BCG segment. A state of a BCG reset flag may be determined, where the BCG reset flag is set to a logical zero when the cross-correlation is above a first threshold, and the BCG reset flag is set to a logical one when the cross-correlation is equal to or below the first threshold. One or more health information for the user may be identified from the BCG reset flag, and at least one of the one or more of the health information may be displayed via a display.

In an embodiment, the received raw motion signal may be filtered prior to generating the BCG segments. The BCG event locations may be generated using a reconstructed signal, where the raw motion signal is decomposed to a decomposed signal, and the decomposed signal is reconstructed to a reconstructed signal.

The raw motion signals may be output via three channels of a three-axis accelerometer, and the present channel may be selected from among the channels using window-based quantification.

In various embodiments of the disclosure, the BCG reset flag may be used to determine a BCG signal quality indicator. The BCG reset flag may also be used to track one or more of the health information comprising: a user's activity level, sleep habits, sleep apnea, sleep efficiency, sleep quality, cardiac arrhythmia detection, and stress monitoring. Furthermore, the BCG reset flag may be used to identify snoring, sleep stage, and also continuously monitor a user's blood pressure and/or a user's heart rate variability. At least some of the health information may be transmitted to another electronic device.

The raw signal from the motion sensor may not be provided if an amount of motion detected in the raw motion signals is higher than a threshold.

Various embodiments of the disclosure may also include an electronic device comprising at least one motion sensor configured to detect raw motion signals for a user and output the raw motion signals as individual channels. The electronic device may comprise a processor configured to monitor the channels for motion activity and select a present channel based on the motion activity.

The electronic device may comprise a transform module configured to transform the raw motion signals to reconstructed signals, where the processor is further configured to determine BCG event locations from the reconstructed signals, generate BCG segments from the raw motion signals using the BCG event locations, and cross-correlate, for the present channel, a first BCG segment to a second BCG segment. The first BCG segment may be one of the BCG segments for the present channel, the second BCG segment is another of the BCG segments for the present channel, and the second BCG segment is immediately after the first BCG segment. The electronic device may also determine a state of a BCG reset flag, where the BCG reset flag is set to a logical zero when the cross-correlation is above a first threshold, and the BCG reset flag is set to a logical one when the cross-correlation is equal to or below the first threshold, and one or more of a health information for the user may be identified from the BCG reset flag.

The electronic device may also comprise a display configured to display at least one of the one or more of the health information.

The electronic device may comprise a filter block configured to filter signals above a first frequency in the received raw motion signal prior to segmenting the raw motion signals. The raw motion signals may be output in three channels by a three-axis accelerometer, and the processor may be further configured to select the present channel from among the channels using window-based quantification.

The transform module may comprise a decomposing module that may be configured to decompose the raw motion signals to a decomposed signal, and a reconstruction module that may be configured to reconstruct the decomposed signals to the reconstructed signal.

The processor may use the BCG reset flag to determine a BCG signal quality indicator, track one or more of the health information comprising: a user's activity level, sleep habits, sleep apnea, sleep efficiency, sleep quality, cardiac arrhythmia detection, stress monitoring, snoring, and sleep stages. The BCG reset flag may also be used to continuously monitor a user's blood pressure and/or a user's heart rate variability. The electronic device may also comprise a transceiver configured to transmit the health information to another electronic device.

Additionally, a raw signal from a motion sensor may not be provided if the amount of motion detected is higher than a second threshold.

While various embodiments of the disclosure have been described above, it should be understood that they have been presented as non-limiting examples only. While the foregoing has been described with reference to certain aspects and examples, it will be understood by those skilled in the art that various changes may be made and equivalents may be substituted without departing from the scope of the disclosure. In addition, many modifications may be made to adapt a particular situation or material to the teachings of the disclosure without departing from its scope. Therefore, it is What are claimed:

1. A method for an electronic device, comprising:
receiving, via at least one motion sensor, channels of raw motion signals for a user;
monitoring the channels for motion activity;
selecting a present channel based on the motion activity;
performing ballistocardiography (BCG) reconstruction for the channels of raw motion signals;
determining BCG event locations from the raw motion signals;
determining, for the channels of reconstructed signals, BCG event locations, wherein each BCG event location is at a respective time point in a respective channel of reconstructed signals;
generating BCG segments from the raw motion signals of the present channel using the BCG event locations, wherein each of the BCG segments comprise a respective time period;
cross-correlating, for the present channel, a first BCG segment to a second BCG segment, wherein the first BCG segment is one of the BCG segments for the present channel, the second BCG segment is another of the BCG segments for the present channel, and the second BCG segment is immediately after the first BCG segment;
determining a state of a BCG reset flag, wherein the BCG reset flag is set to a logical zero when the cross-correlation is above a first threshold, and the BCG reset flag is set to a logical one when the cross-correlation is equal to or below the first threshold;
identifying one or more of a health information for the user from the state of the BCG reset flag; and
displaying at least one of the one or more of the health information on a display.

2. The method of claim 1, comprising filtering signals above a first frequency in the raw motion signals prior to generating the BCG segments.

3. The method of claim 1, wherein the motion sensor is a three-axis accelerometer.

4. The method of claim 1, wherein the present channel is selected from among the channels using window-based quantification.

5. The method of claim 1, wherein the BCG event locations are generated using reconstructed signals, comprising:
decomposing the raw motion signals to decomposed signals, and
reconstructing the decomposed signals to the reconstructed signals.

6. The method of claim 1, wherein the BCG reset flag is used to track one or more of the health information comprising: a user's activity level, sleep habits, sleep apnea, sleep efficiency, sleep quality, cardiac arrhythmia detection, and stress monitoring.

7. The method of claim 1, wherein the BCG reset flag is used to determine a BCG signal quality indicator.

8. The method of claim 1, wherein the BCG reset flag is used to identify one or both of: snoring and sleep stage.

9. The method of claim 1, wherein the BCG reset flag is used to continuously monitor one or more of: a user's blood pressure, a user's heart rate variability.

10. The method of claim 1, comprising transmitting the health information to another electronic device.

11. An electronic device, comprising:
at least one motion sensor configured to detect respective raw motion signals for a user and output each of the respective raw motion signals as respective individual channels;
a processor configured to:
monitor the channels for motion activity; and
select a present channel based on the motion activity;
a transform module configured to transform the channels of raw motion signals to channels of reconstructed signals, wherein the processor is further configured to:
determine, for the channels of reconstructed signals, ballistocardiography (BCG) event locations, wherein each BCG event location is at a respective point in time in a respective channel of reconstructed signals;
generate BCG segments from the raw motion signals of the present channel using the BCG event locations, wherein each of the BCG segments comprise a respective time period;
cross-correlate, for the present channel, a first BCG segment to a second BCG segment, wherein the first BCG segment is one of the BCG segments for the present channel, the second BCG segment is another of the BCG segments for the present channel, and the second BCG segment is immediately after the first BCG segment;
determine a state of a BCG reset flag, wherein the BCG reset flag is set to a logical zero when the cross-correlation is above a first threshold, and the BCG reset flag is set to a logical one when the cross-correlation is equal to or below the first threshold; and
identify one or more of a health information for the user from the state of the BCG reset flag; and
a display configured to display at least one of the one or more of the health information.

12. The electronic device of claim 11, comprising a filter block configured to filter signals above a first frequency in the raw motion signals prior to segmenting the raw motion signal.

13. The electronic device of claim 11, wherein the at least one motion sensor is a three-axis accelerometer.

14. The electronic device of claim 11, wherein the processor is configured to select the present channel from among the channels using window-based quantification.

15. The electronic device of claim 11, wherein the transform module comprises:
a decomposing module configured to decompose the raw motion signals to a decomposed signal, and
a reconstruction module configured to reconstruct the decomposed signals to the reconstructed signal.

16. The electronic device of claim 11, wherein the processor is configured to use the BCG reset flag to track one or more of the health information comprising: a user's activity level, sleep habits, sleep apnea, sleep efficiency, sleep quality, cardiac arrhythmia detection, and stress monitoring.

17. The electronic device of claim 11, wherein the processor is configured to use the BCG reset flag to determine a BCG signal quality indicator.

18. The electronic device of claim 11, wherein the processor is configured to use the BCG reset flag to identify one or both of: snoring and sleep stage.

19. The electronic device of claim 11, wherein the processor is configured to use the BCG reset flag to continuously monitor one or more of: a user's blood pressure, a user's heart rate variability.

20. The electronic device of claim 11, comprising a transceiver configured to transmit the health information to another electronic device.

* * * * *